United States Patent
Kyriakou

(12) 
(10) Patent No.: US 9,427,200 B2
(45) Date of Patent: Aug. 30, 2016

(54) DETERMINATION OF PHYSIOLOGICAL CARDIAC PARAMETERS AS A FUNCTION OF THE HEART RATE

(71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 214 days.

(21) Appl. No.: 14/222,345

(22) Filed: Mar. 21, 2014

(65) Prior Publication Data

US 2015/0265234 A1    Sep. 24, 2015

(51) Int. Cl.
| | |
|---|---|
| *A61B 6/00* | (2006.01) |
| *A61B 6/03* | (2006.01) |
| *A61B 5/024* | (2006.01) |
| *A61N 1/365* | (2006.01) |
| *A61B 5/00* | (2006.01) |

(52) U.S. Cl.
CPC .............. *A61B 6/503* (2013.01); *A61B 6/032* (2013.01); *A61B 6/481* (2013.01); *A61B 6/504* (2013.01); *A61B 6/5217* (2013.01); *A61N 1/36578* (2013.01); *A61B 5/024* (2013.01); *A61B 5/7289* (2013.01); *A61B 6/4441* (2013.01)

(58) Field of Classification Search
CPC .. A61B 6/032; A61B 6/4208; A61B 6/4233; A61B 6/4441; A61B 6/481; A61B 6/503; A61B 6/504; A61B 6/5217
USPC ........... 378/4, 8, 62, 196–198; 382/130, 131
See application file for complete search history.

(56) References Cited

U.S. PATENT DOCUMENTS

| | | | | | |
|---|---|---|---|---|---|
| 5,433,199 | A | * | 7/1995 | Cline | G01R 33/5608 600/413 |
| 5,458,126 | A | * | 10/1995 | Cline | G01R 33/56325 324/309 |
| 6,154,516 | A | * | 11/2000 | Heuscher | A61B 6/032 378/15 |
| 6,249,693 | B1 | * | 6/2001 | Cline | G01R 33/56 600/410 |
| 6,793,496 | B2 | * | 9/2004 | Edic | G06T 11/006 434/262 |
| 7,471,767 | B2 | * | 12/2008 | Spahn | G03B 42/02 378/101 |
| 7,526,112 | B2 | * | 4/2009 | Murphy | G06T 7/0012 128/922 |
| 7,668,290 | B2 | * | 2/2010 | Tanaka | A61B 6/504 378/62 |
| 7,835,496 | B2 | * | 11/2010 | Maschke | A61B 6/467 378/62 |
| 8,208,991 | B2 | * | 6/2012 | Markowitz | A61B 5/0422 600/424 |
| 8,244,013 | B2 | * | 8/2012 | Galant | G06T 7/0081 378/4 |
| 8,560,968 | B1 | * | 10/2013 | Nair | G06F 19/3406 715/810 |

(Continued)

FOREIGN PATENT DOCUMENTS

| | | |
|---|---|---|
| DE | 102012205935 | 10/2013 |
| DE | 102012216652 | 3/2014 |

OTHER PUBLICATIONS

Sabee Molloi et al., "Quantification of Coronary Artery Lumen Volume by Digital Angiography: In Vivo Validation," Circulation 104. 2351-2357, 2001.*

(Continued)

*Primary Examiner* — Allen C. Ho
(74) *Attorney, Agent, or Firm* — Lempia Summerfield Katz LLC

(57) ABSTRACT

A method for determining physiological cardiac parameters as a function of a heart rate is provided. For at least two heart rates adjusted by a cardiac stimulation during the recording, in each case, a four-dimensional image data set of the heart showing the entire cardiac cycle is recorded using an X-ray device. The physiological cardiac parameters are determined by evaluation of the four-dimensional image data sets.

24 Claims, 3 Drawing Sheets

(56) References Cited

U.S. PATENT DOCUMENTS

| | | | | |
|---|---|---|---|---|
| 9,036,780 | B2* | 5/2015 | Kyriakou | A61B 5/7289 |
| | | | | 378/62 |
| 9,123,148 | B2* | 9/2015 | Kyriakou | G06T 17/00 |
| 9,141,763 | B2* | 9/2015 | Sharma | G06F 19/3437 |
| 9,189,848 | B2* | 11/2015 | Sakaguchi | G06T 7/0014 |
| 2008/0171931 | A1* | 7/2008 | Maschke | A61B 5/055 |
| | | | | 600/410 |
| 2009/0198121 | A1* | 8/2009 | Hoheisel | A61B 6/504 |
| | | | | 600/410 |
| 2013/0336450 | A1 | 12/2013 | Kyriakou et al. | |
| 2014/0081131 | A1 | 3/2014 | Kyriakou | |
| 2014/0094680 | A1* | 4/2014 | Kowarschik | A61B 6/507 |
| | | | | 600/407 |

OTHER PUBLICATIONS

Graeme C. McKinnon et al., "Towards Imaging the Beating Heart Usefully with a Conventional CT Scanner", IEEE Transactions on Biomedical Engineering, Feb. 1981, pp. 123-127, vol. BME-28, No. 2.

Guang-Hong Chen et al., "Prior Image Constrained Compressed Sensing (PICCS): A Method to Accurately Reconstruct Dynamic CT Images from Highly Undersampled Projection Data Sets", Med. Phys., Feb. 2008, pp. 660-663, vol. 35, No. 2.

Suzana Gligorova et al., "Pacing Stress Echocardiography", Cardiovascular Ultrasound, BioMed Central, 3:36, pp. 1-11, 2005, htt://www.cardiovascularultrasound.com/content/3/1/36; 2005.

* cited by examiner

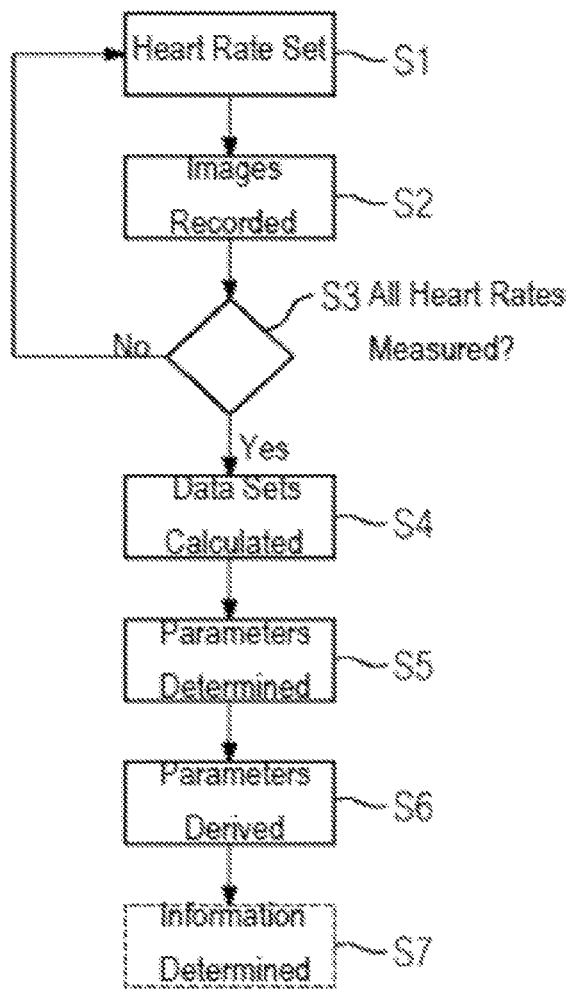
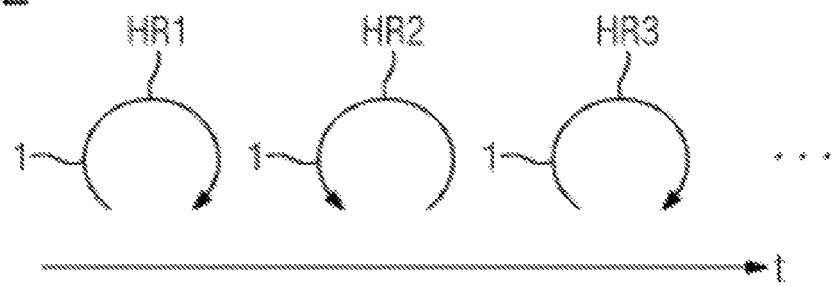

DETERMINATION OF PHYSIOLOGICAL CARDIAC PARAMETERS AS A FUNCTION OF THE HEART RATE

BACKGROUND

The present embodiments relate to determination of physiological cardiac parameters as a function of heart rate.

In the field of angiography, a number of techniques are known for obtaining information about a patient's heart. Most images (e.g., X-ray images) of the heart are taken using the technique of digital subtraction angiography (DSA). DSA involves a contrast agent being administered to the patient such that, on images of the heart, the blood vessels filled with contrast agent and the heart filled with contrast agent may be distinguished clearly. If mask images that had been taken before the contrast agent was introduced into the region to be X-rayed in a patient who, compared to the situation with the contrast images, has not been moved, are subtracted from the images taken using contrast agent (e.g., "contrast images"), all that remains, apart from noise effects, are signal components of the contrast agent. An excellent evaluation of the resulting DSA images may thus be possible.

DSA is not only used in cases where a detailed mapping or a detailed evaluation of a patient's cardiovascular structure is to be provided, but also when dynamic information relating to the heart (e.g., a cardiac motion analysis) is to be acquired. Alongside two-dimensional digital subtraction angiography, the reconstruction of three-dimensional reconstructed data sets for various cardiac phases from two-dimensional projection images has also been suggested. A four-dimensional angiography data set showing the motion of the heart and the surrounding blood vessels throughout an entire cardiac cycle is thus generated, consequently showing a three-dimensional volume pumped throughout a cardiac cycle. The fourth dimension in such image data sets relates to the time factor.

In order to record such four-dimensional angiography image data sets, an X-ray device with, for example, a C-arm may be used in an angiography unit. This involves recording projection images in various projection directions at various points of time in the cardiac cycle. The projection images recorded are assigned to different cardiac phases (e.g., time periods in the cardiac cycle), which provides that the cardiac cycle is broken up into different time segments. Each set of projection images recorded within a time segment is sorted into a group of projection images. Each of these groups of projection images is used to generate a three-dimensional reconstruction image data set assigned in each case to the time segment. If these three-dimensional reconstruction image data sets are now put together according to the time order for the cardiac cycle, the four-dimensional angiography image data set is generated.

In order to counteract effects due to irregularity in cardiac motion and the such, US 2013/0336450 A1, issued as U.S. Pat. No. 9,036,780 B2 on May 19, 2015, proposes that projection images be recorded such that at least one recording parameter describing the time progression in the recording of the projection images is selected as a function of a cardiac stimulation carried out to provide a stable heart rate during the recording such that the recording of the projection images is synchronized with the cardiac cycle. Thus, by skillful selection of the recording time and/or of the movement of the C-arm, it therefore becomes possible to synchronize the time progression (e.g., the "timing") of the recording of the projection images with the cardiac cycle such that the projection images for each time segment in the cardiac cycle are recorded. The projection images are thus distributed equally over the projection directions. A complete reconstruction for the individual cardiac phases may be achieved with as few artifacts as possible.

A known method of producing a stable heart rate is carrying out "pacing". In connection with the recording of four-dimensional image data sets, "slow cardiac pacing", where the heart rate tends to be in the lower range (e.g., lower than 140 beats per minute (bpm)) is provided, such that the significance of induced ventricular tachycardia is extremely slight. In this way, "ventricular flutter" is avoided.

Cardiac investigations including four-dimensional digital subtraction angiography, for example, aim to obtain prognostic cardiac diagnostic parameters that may predict the extent and severity of the disease, a risk of cardiac infarction and the like. Such known diagnostic parameters are, for example, the Duke score, the WMSI score (e.g., peak wall motion score index), the relationship between force (e.g., contraction) and heart rate, described by the Bowditch effect, the systolic volume index, the cardiac ejection fraction (EF), cardiac perfusion parameters and the like. In order to be able to calculate these diagnostic parameters, various physiological cardiac parameters (e.g., cardiac parameters relating to the heart wall that may be acquired from a segmentation of the heart muscle, parameters relating to the lumen and parameters relating to the heart's dynamics) may be provided.

Most of these cardiac parameters and diagnostic parameters are also dependent on the frequency of the heartbeat (e.g., heart rate). In order to make it possible to obtain the cardiac parameters and from these the diagnostic parameters also at other heart rates (e.g., at higher heart rates), it is known practice, for example, to administer drugs that stimulate the heart rate so that magnetic resonance images and/or ultrasound images of the heart and surroundings of the heart may be generated. For example, the method of pacing stress echocardiography is known in the field of ultrasound. However, this only allows numerical determinations of cardiac parameters for various heart rates to be carried out. In an angiography unit, however, C-arm X-ray devices are more common because C-arm X-ray devices provide the option of digital subtraction angiography.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for precise and controlled determination of physiological cardiac parameters for different heart rates using an X-ray device is provided.

In one embodiment, for each of at least two heart rates set by cardiac stimulation, using an X-ray device, a respective four-dimensional image data set of the heart showing an entire cardiac cycle is recorded. The physiological cardiac parameters are determined by evaluation of the image data sets.

A plurality of four-dimensional angiography image data sets is recorded using an X-ray device at different heartbeat frequencies (e.g., heart rates) within a series of recordings, such that a plurality of physiological cardiac parameters and prognostic diagnostic parameters obtained from these may be acquired.

With the heart rate, a fifth dimension is added to the image data that has been acquired, allowing the calculation of additional diagnostic parameters that are dependent on the heart rate (e.g., of a Duke score). After heart rates have been specifically adjusted by cardiac stimulation during the recording, there is a reproducibility of the measurements, according to which the same conditions may be reproduced. Consequently, physiological cardiac parameters and also diagnostic parameters derived therefrom (e.g., functional and/or prognostic diagnostic parameters) may be determined directly in the angiography unit using an X-ray device (e.g., using a C-arm X-ray device during the investigation of a coronary heart disease). The physiological cardiac parameters, which may be time-dependent in the sense of being dependent on the cardiac phase in the cardiac cycle, are thus also provided as a function of the heart rate (e.g., as five-dimensional information) and may be further evaluated both diagnostically and therapeutically. The presence of five-dimensional data has the advantage that more image data is available overall, such that this data may be interrelated and used for the reciprocal improvement of reconstructions and suchlike, which will be described in greater detail hereafter.

The procedure according to one or more of the present embodiments also includes the calculation of the usual angiography image data sets (e.g., the calculation of four-dimensional coronary angiography image data sets), and additionally offers an improved determination of physiological cardiac parameters as a function of the heart rate, such that overall a combination of a kind that hitherto could only be achieved in the prior art by a plurality of image recordings using different methods is produced. The method according to one or more of the present embodiments therefore provides a reproducible, heart-rate dependent functional imaging of the heart (e.g., using an X-ray device that has a C-arm).

The physiological cardiac parameters may thus be determined at least partially in a time-dependent manner in the sense of a dependence on the point or segment of time (e.g., cardiac phase) in the cardiac cycle, and/or may form a dynamic model of the heart, and/or at least one cardiac parameter related to the heart wall (e.g., a wall thickness), and/or at least one cardiac parameter related to the lumen (e.g., the volume of the lumen). Additionally or alternatively, at least one cardiac parameter related to cardiac perfusion may be determined as cardiac parameters. As already mentioned, the values that form the basis of the investigation of, for example, prognostic diagnostic parameters that may be derived from the physiological cardiac parameters are, for example, the progression of parameters for the heart wall (e.g., the heart muscle) and the lumen during the cardiac cycle, which consequently correspond in time-dependence to a diagram of the dynamics of the heart at the respective heart rate (e.g., to a dynamics model). In one embodiment, the preferred location-dependent wall thickness of the heart and/or the volume of the lumen will be used across the cardiac cycle in a time-dependent manner. One or more of the present embodiments also provide the option of using the heart rate as a further, fifth dimension, such that a dependence related thereto is also known.

This makes it possible in an advantageous manner to determine from the cardiac parameters at least one diagnostic parameter (e.g., a prognostic parameter such as a Duke score and/or a WMSI score and/or a Bowditch effect and/or a systolic volume index and/or a cardiac ejection fraction (EF) and/or a contraction force-frequency relationship). The analysis of the heart wall, of the lumen, and optionally of further characteristics relating to the heart (e.g., the physiological cardiac parameters) provides the essential input for the calculation of the diagnostic parameters. These depend in fact on the heart rate, and the nature of the dependence on the heart rate leads to different prognoses for the patient's condition.

The heart rate may be adjusted by intra-cardiac pacing (e.g., using a pacing catheter) and/or by extra-cardiac pacing (e.g., using a cardiac pacemaker). Provision can therefore be made, before carrying out the method according to one or more of the present embodiments, for a pacing catheter to be introduced into the right ventricle of the patient's heart, for example, in order to achieve the desired heart rates by controlling the pacing catheter accordingly. A further pacing option is the use of a cardiac pacemaker, which falls into the category of extra-cardiac pacing (e.g., pacing from outside the heart). These techniques are known in principle in the prior art.

In one embodiment, the heart rate may be increased in fixed, predetermined steps and/or heart rates in the range from 80 to 220 bpm (e.g., in the range from 80 to 140 bpm) to be used. The recording sequence for the method according to one or more of the present embodiments may therefore start, for example, at a heart rate that is higher than the spontaneous heart rate (e.g., 80 to 90 bpm). After each recording of a four-dimensional image data set, the heart rate is increased by a defined step. Contrast agent may be administered separately for each heart rate. In one embodiment, a plurality of different heart rates may be measured after an administration of contrast agent. Specific image-recording protocols are dealt with in greater detail hereafter. In order to keep the amount of contrast agent that is to be administered to a patient as low as possible, the number of heart rates that are to be measured may be limited (e.g., to three to five heart rates that may be adjusted so that the heart rates are separated by equal intervals by increasing the heart rate in steps).

This involves digital subtraction angiography images, (e.g., at least images recorded after the administration of a contrast agent). The recording of the four-dimensional image data sets may take place after an administration of contrast agent. In one embodiment, a fresh administration of contrast agent may take place for each heart rate, or a plurality of heart rates may be measured after an administration of contrast agents. In this context (e.g., when cardiac perfusion is to be investigated as a physiological cardiac parameter), at least one late-enhancement image data set may be recorded for each heart rate. By appropriate timing and delayed recording, it is consequently possible to determine a "first-pass" and a "late-enhancement" cardiac perfusion as a function of the heart rate. As a result of heart rates being specifically adjusted by cardiac stimulation (e.g., pacing), these recordings are in principle repeatable and reproducible. This also allows extensive comparability of the records. Late-enhancement image data sets may be recorded (e.g., 10 to 30 minutes after first-pass-image data sets and show typical properties of scar tissue and suchlike).

In one embodiment, the four-dimensional image data sets may be acquired by reconstruction of a plurality of three-dimensional image data sets out of two-dimensional projection images for different projection directions taken at the same phase of the cardiac cycle using an image-recording arrangement including an X-ray detector and an X-ray emitter, and by combination of the three-dimensional image data sets. In order to generate four-dimensional angiography image data sets, projection images are therefore frequently recorded from different projection directions. The projection images may be assigned to the cardiac phases. A sufficient number of projection images may thus be available for each cardiac phase so that a reliable reconstruction of a three-dimensional image data set that relates to this cardiac phase is then available. Various techniques are known that also enable projection images from other cardiac phases to influence the reconstruction of a three-dimensional image data set for a cardiac phase (e.g., by a three-dimensional reconstruction data set first being generated from all the projection images, structural information about the heart that may be taken into account as boundary conditions in the reconstruction of the three-dimensional image data sets already having been derived from the data set). If the three-dimensional image data sets are ordered according to the cardiac cycle, the dynamic, four-dimensional angiography image data set is generated. The number of cardiac phases and the precise definition thereof (e.g., the time segment of the cardiac cycle that the cardiac phase corresponds with) may be predetermined or set by a user.

In one embodiment, the projection images for the various cardiac phases may be recorded during one rotation of the recording arrangement. A recording parameter describes the time progression during the recording of the projection images for a heart rate being selected as a function of the heart rate, such that the recording of the projection images is synchronized with the cardiac cycle. This procedure, which may also be implemented in the context of one or more of the present embodiments, is disclosed by U.S. Patent Publication No. 2013/0336450 A1 (DE 10 2012 205 935 A1), issued as U.S. Pat. No. 9,036,780 B2 on May 19, 2015, the disclosure of which is hereby incorporated by reference in its entirety. In this context, for example, a projection image may be recorded for each cardiac phase in each cardiac cycle (e.g., a recording frequency of the projection images may be selected as a whole number multiple of the heart rate). After the heart rate in the recording sequence of the method according to one or more of the present embodiments has been changed, the synchronization is adjusted to each heart rate that has been re-set. For example, the recording speed and/or the speed of movement of the recording arrangement may be adjusted to a re-set heart rate.

Various possibilities for the specific sequence of the recordings in the individual four-dimensional angiography image data sets (e.g., the movement of a C-arm that supports the recording arrangement) may be provided. In one embodiment, for each heart rate set, a rotational movement of the recording arrangement covering predefined projection directions (e.g., 180° plus the fan angle) is carried out, and opposing movement directions of the recording arrangement are used in each case for consecutive recordings at different heart rates. In one embodiment, the X-ray detector and the X-ray emitter rotate round the target region (e.g., the heart). For a complete reconstruction satisfying Tuy's condition, an angular range of 180° plus the fan angle is to be covered when the geometry is that of a fan-shaped beam. The recording arrangement may traverse the same recording trajectory for each heart rate. For example, for the recording trajectory, consecutive heart rates may always be traversed in the opposite direction. An automatic triggering of the recording may be provided, yet there may be manual triggering (e.g., as a function of a previously, manually triggered administration of contrast agent). In one embodiment, partial rotations may be carried out (e.g., 180° plus the fan-beam angle). In another embodiment, each heart rate may also provide a full rotation, either automatically or manually triggered.

In one embodiment, the projection images for all heart rates may be recorded during a single, continuous rotation of the recording arrangement around the patient (e.g., for the change in the heart rate to be effected while the recording arrangement is moving). In one embodiment, a continuous movement of the recording arrangement, during which the change in the heart rate may also take place, may be provided. The data recording and reconstruction may be synchronized retroactively using an appropriate reconstruction window. When the heart rate is changed, at least one recording parameter describing the temporal progression may also be adjusted during the recording of the projection images.

In one embodiment, projection images of other cardiac phases and/or of other heart rates are taken into consideration in the reconstruction of the three-dimensional image data sets. Due to the basic comparability of the heart movements at different heart rates, projection images for other heart rates will provide information (e.g., for the same cardiac phase) that may improve the reconstruction of three-dimensional image data sets for the cardiac phases at other heart rates. By taking into account further image data available, noise effects and other artifacts in the image data sets may, for example, be reduced.

This is advantageous, for example, when the reconstruction is carried out as an iterative reconstruction, in which the projection images for other cardiac phases and/or other heart rates involve at least one boundary condition and/or the target function. Iterative reconstructions methods use a priori information in order to achieve an improved reconstruction of three-dimensional image data sets for the cardiac phases.

When information from other projection images is used, information derived from the projection images is included (e.g., information relating to movement such as motion vector fields and data as to how far certain features usually move). Known algorithms from the field of the reconstruction of four-dimensional angiography image data sets encompass, for example, the McKinnon-Bates algorithm and the Piccs algorithm. The subsequently published document DE 10 2012 216 652 A1 describes a further option for improving the reconstruction of 4D volumes, whereby voxels are treated differently according to motion variability and change variability. A comparative reconstruction may be effected taking into account all the projection images for a heart rate and/or all projection images for a cardiac phase at all heart rates.

The fact that a very much greater number of image data is available and that image data for other heart rates may be used to draw conclusions relating to image data for a heart rate that has been observed may also be used to reduce the patient's exposure to radiation. Thus, in one embodiment, the dose may be reduced in comparison with the image recording for the first heart rate for at least one recording procedure after the recording for the first heart rate (e.g., for all recording procedures after the recording for the first heart rate). In the procedure, at least projection images from recordings for the first heart rate are taken into account in the reconstruction of the three-dimensional image data sets for later heart rates. Thus, the dose setting may be varied according to the information collected on the anatomy and on the motion sequences in order to keep the patient's exposure to radiation as low as possible. For example, the recording may be carried out with the full dose of X-rays in the case of the first heart rate, and only 75% of this dose of X-rays for the second heart rate, only 50% for the third heart rate and so forth, may be used. In one embodiment, the dose may be reduced in steps.

In order to determine the specific cardiac parameters, the four-dimensional image data sets may be segmented (e.g., according to the cardiac wall and the lumen). Such segmentation procedures are already known in principle from the prior art and do not need to be described in further detail here. The usual segmentation tools and such may thus be used.

In one embodiment, cardiac parameters for heart rates that have not been measured may be determined by interpolation and/or extrapolation from the cardiac parameters for measured heart rates and/or from the four-dimensional image data sets and/or from heart motion vector fields derived therefrom. The five-dimensional information available may thus also be used to approximate the behavior of the heart at heart rates that have not been measured. One option for this is, for example, interpolation between "motion vector fields". Appropriate interpolation methods may be used, for example, between the corresponding motion vectors. An interpolation or extrapolation using derived diagnostic parameters themselves may also be provided by, for example, estimating the progression of the function of the diagnostic parameter in relation to the heart rate using a fit. Such a procedure may also be provided for physiological cardiac parameters.

In the interpolation or extrapolation of cardiac motion vector fields, an interpolation or extrapolation of the image information relating to the four-dimensional image data sets may be taken into account as a boundary condition and/or as a penalty component during an optimization procedure. This provides that the image information contained in the four-dimensional image data sets may also be used to improve the interpolation or extrapolation (e.g., as a penalty component in a corresponding minimization procedure).

In addition to the method, an X-ray device including, for example, a recording arrangement provided on a C-arm, having an X-ray emitter and an X-ray detector, is provided. The X-ray device also includes a control device configured for carrying out the method according to one or more of the present embodiments. All the details relating to the method may be applied by analogy to the X-ray device. The X-ray device may also include a cardiac stimulation device (e.g., a pacing catheter and/or a cardiac pacemaker) or a special interface with a cardiac stimulation device, such that information about the heart rate may be obtained and/or that control of the cardiac stimulation device becomes possible using the control device. Such an X-ray device may also include a contrast agent injector that may also be controlled by the control device. The control device can thus include, for example, an image-recording unit to control the recording arrangement for recording the four-dimensional image data sets and also a unit for determining the cardiac parameters.

BRIEF DESCRIPTION OF THE DRAWINGS

FIG. 1 shows a flow diagram of one embodiment of a method;

FIG. 2 shows a first option for moving an image recording arrangement during recording of projection images;

DETAILED DESCRIPTION

Figure 3:
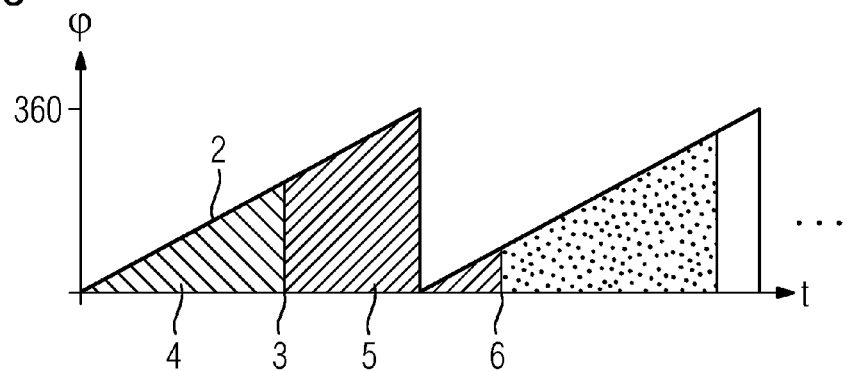
FIG. 3 shows a second option for moving the image recording arrangement during the recording of the projection images.

FIG. 1 shows a flow diagram of an exemplary embodiment of a method, where cardiac stimulation to adjust heart rates is also shown. Before the method is begun, a patient is positioned in an X-ray device (e.g., in an X-ray device having a C-arm, on which an X-ray emitter and an X-ray detector are arranged facing each other). Before projection images are recorded, in act S1, a first heart rate is set. The first heart rate is higher than a usual resting heart rate. In one embodiment, 80 bpm is selected as the first heart rate. The adjustment of the heart rate in the patient may be achieved, for example, by cardiac stimulation using a pacing catheter that is located in the heart, or using a cardiac pacemaker.

If the heart rate in act S1 is set at a stable rate, then in act S2, projection images for the patient are recorded from different projection directions, and such that the recording of the projection images is synchronized with the cardiac cycle. In practical terms, this provides that the projection images for each cardiac phase (e.g., for each time segment in the cardiac cycle) are recorded such that the projection images are equally distributed with respect to the projection directions, such that a complete reconstruction of three-dimensional image data sets with a minimized number of artifacts may be achieved for the individual cardiac phases. The recording frequency for the projection images is selected as a whole-number multiple of the heart rate, such that the whole-number multiple consequently indicates how many images are to be recorded per cardiac cycle. The temporal synchronization may be selected, for example, such that 30 to 40 projection images are recorded for each cardiac phase.

The projection images in act S2 are recorded after administration of a contrast agent as is known in principle. Not only is the recording frequency selected based on the heart rate, but the X-ray dose is also reduced with every heart rate after the first heart rate in order to keep the patient's exposure to radiation as low as possible.

In act S3, a check is carried out to see whether all the heart rates have been measured. If this is not the case, then the procedure continues in act S1 with the next heart rate. In one embodiment, four heart rates that are spaced an equal distance apart (e.g., heart rates of 80 bpm, 100 bpm, 120 bpm and 140 bpm) are measured.

There are a number of options that may be provided for the specific selection of the recording trajectory of the recording arrangement including an X-ray detector and X-ray emitter and for the temporal progression. As shown in FIG. 2, identical recording trajectory 1 may be used for each heart rate, HR1, HR2, and so on. In order to save the effort involved in moving the C-arm, this recording trajectory 1 is traversed in constantly changing directions, as the arrows on the recording trajectory 1 in FIG. 2 show. In this procedure, the changeover of heart rates and the start of the respective image-recording process may be triggered either automatically or manually. Manual triggering is useful, for example, when fresh contrast agent is administered for each heart rate (e.g., a procedure that may also be triggered manually). Automatic triggering may also be provided.

In some embodiments, a single administration of contrast agent is sufficient, and the recording of the projection images ensues during a continuous rotational movement of the C-arm, as shown in greater detail in FIG. 3. As shown from the progression 2 in the angulation φ of the C-arm over time, there is a continuous rotation of the C-arm. At a point in time 3, there are sufficient projection images for the first heart rate, for example, after an angular range of 200° (e.g., 180° plus fan angle) has been covered. This provides that the projection images recorded in field 4 are assigned to the first heart rate. At the point in time 3, there is a switch over to a second heart rate, and in the field 5, projection images for the second heart rate are recorded for an angular interval of the same size. At the point in time 6, there is then a switch over to a third heart rate that continues accordingly in the further progression. Consequently, optimum use of time is provided, also allowing, for example, for the image-recording procedure to be terminated altogether during one single administration of contrast agent.

When there is a change in the heart rate, recording parameters may also be changed. For example, the recording frequency may be adjusted to synchronize with the heart rate, and/or the X-ray dose may be reduced (e.g., in steps). A reduction in the X-ray dose (e.g., 100% for the first heart rate, 75% for the second heart rate, 50% for the third heart rate and 25% for the fourth heart rate) is therefore possible, since information from the recordings for other heart rates may be taken into account in the reconstruction for later heart rates.

In act S4 (see again FIG. 1), four-dimensional angiography image data sets for each heart rate are calculated from the recorded projection images for the heart rates. Act S4 may also be carried out "online" directly after act S2, due to the use of image data for other heart rates in the reconstruction, which will be explained hereafter in greater detail. In one embodiment, the calculation of the four-dimensional image data sets may be carried out only when the projection images for all the heart rates have been recorded.

The calculation of the four-dimensional image data sets is carried out such that the projection images for each cardiac phase are used to reconstruct a three-dimensional image data set for this phase in an iterative manner, and the three-dimensional image data sets are put together to form the four-dimensional angiography image data set for the entire cardiac cycle.

In the reconstruction of three-dimensional image data sets for specific cardiac phases at a specific heart rate, it is not only, as is already known in principle, projection images or information relating to other cardiac phases derived therefrom that are taken into consideration for the improvement of the image quality, but also projection images for other heart rates. All these are incorporated into the iterative reconstruction that is based on a priori information. Seeing that excellent a priori information is already available as a result of the plurality of projection images, and the measurements for different heart rates are readily comparable, mainly due to the synchronization, this provides an excellent basis that allows among other things for the dose to be reduced for subsequent heart rates. By taking into consideration the projection images for other cardiac phases and heart rates, this allows a reduction in noise and other artifacts in the image data sets.

Figure 4:
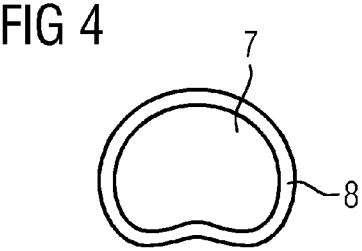
FIG. 4 shows a diagram illustrating exemplary segmentation in determination of physiological cardiac parameters.

In act S5, physiological cardiac parameters that, for example, describe the behavior of the cardiac wall (e.g., of the heart muscle) and of the lumen across the cardiac cycle for different heart rates, in the style of a dynamic model of the heart, are then determined. In order to determine the corresponding cardiac parameters that consequently relate to the cardiac wall and the lumen, in act S5, a segmentation of the four-dimensional angiography image data sets according to the lumen 7 and the cardiac wall 8 is carried out, as indicated by FIG. 4. For this, the usual segmentation methods, which are known in principle, may be used, and the parameters determined may be positions of the cardiac wall 8, the thickness of the cardiac wall 8, the volume of the lumen 7, fields of motion (e.g., sets of motion vectors for at least some of the voxels), and so on. However, this differs from the prior art in that a five-dimensional dynamic model, in which the heart rate consequently forms the fifth dimension, is available.

Figure 5:
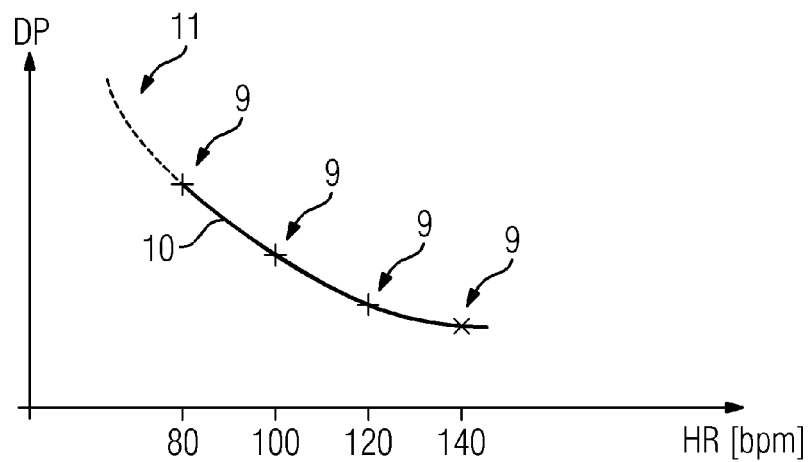
FIG. 5 shows an exemplary diagnostic parameter that is dependent on the heart rate.

In act S6, various diagnostic parameters of the heart (e.g., prognostic diagnostic parameters) that may include a Duke score, a WMSI score, a Bowditch effect, a contraction force-frequency relationship, a systolic volume index, a cardiac ejection fraction (EF), cardiac perfusion parameters and suchlike, are derived from the cardiac parameters (e.g., from the five-dimensional dynamic model). FIG. 5 shows a possible result. FIG. 5 shows a diagnostic parameter DP plotted against the heart rate HR. The four measuring points 9 are visible for the heart rates that have been measured (e.g., 80, 100, 120 and 140 bpm). Using a fit or other interpolation, a curve 10 may be drawn between the heart rates measured. Optionally, an extrapolation may also be carried out in a field 11.

Figure 6:
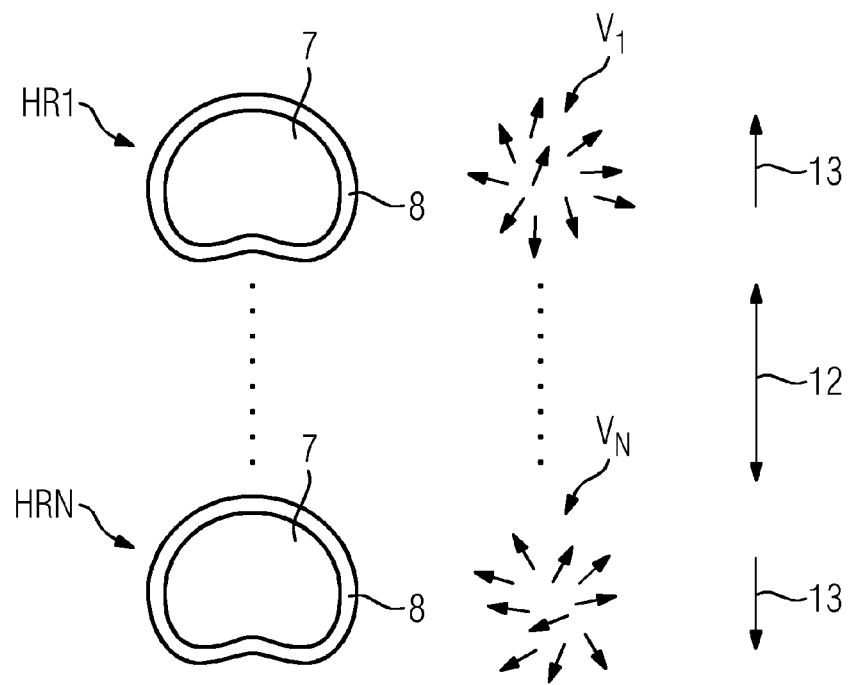
FIG. 6 shows a diagram illustrating exemplary interpolation between motion vector fields.

In one embodiment, information on heart rates that have not been measured may be determined with the cardiac parameters determined in act S7 using the four-dimensional angiography image data sets and/or of the dynamic model. This is because an interpolation and/or extrapolation may already be carried out in this region (e.g., for the cardiac parameters for heart rates that have not been measured), as is indicated in FIG. 6. In FIG. 6, both the cardiac wall 8 and the lumen 7 are shown in diagram form for the first heart rate measured HR1 and for the last heart rate measured HRN, as are the motion vector fields $V_1$ and $V_N$. An interpolation may be carried out between all the heart rates recorded there according to the arrow 12. However, an extrapolation may also be provided according to the arrows 13. If, for example, an interpolation or extrapolation of the motion vectors for the motion vector field V is to be carried out, this may be achieved in an optimization process, in which interpolations of image data for the four-dimensional image data sets may be taken into account (e.g., as a penalty component). Such interpolated and/or extrapolated cardiac parameters may ultimately also be used to calculate diagnostic parameters for other heart rates.

In one embodiment, "late-enhancement" image data sets may be recorded in addition to "first pass" image data sets (e.g., if cardiac parameters relating to cardiac perfusion are to be determined).

The cardiac parameters and/or diagnostic parameters determined may be displayed to a user in an appropriate manner.

Figure 7:
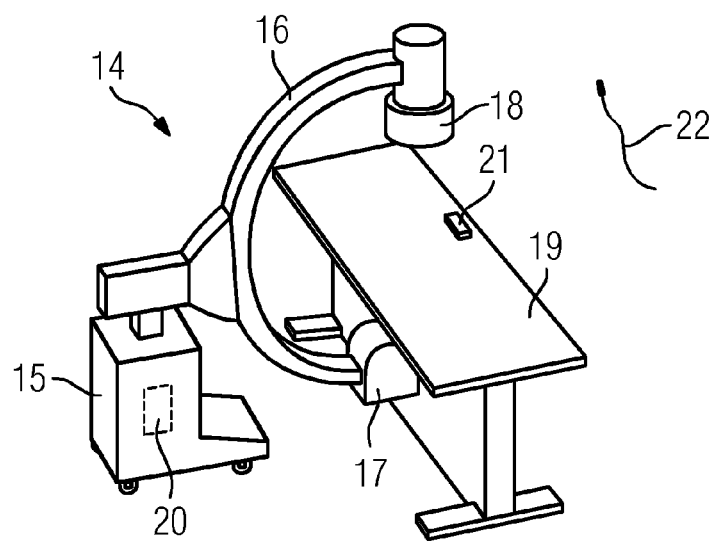
FIG. 7 shows one embodiment of an X-ray device.

FIG. 7 shows one embodiment of an X-ray device 14. The X-ray device 14 includes, for example, a C-arm 16 mounted on a stand 15, an X-ray emitter 17 and an X-ray detector 18 arranged facing each other on the C-arm 16. The C-arm 16 is rotatably mounted such that the C-arm 16 may be pivoted round a patient placed on a patient couch 19. The operation of the X-ray device 14 is controlled by a control device 20, which is merely indicated in FIG. 7. The control device 20 is configured to carry out the method according to one or more of the present embodiments. For this purpose, the control device 20 is also configured to control a contrast agent injector 21 that is assigned to the X-ray device 14 and a pacing catheter 22 that is to be used for cardiac stimulation.

Thus, a fully automatic implementation of the method including the adjustment of the heart rates and the administration of the contrast agent may be achieved.

Although the invention has been illustrated and described in more detail using the exemplary embodiments, the invention is not restricted by the disclosed examples. Other variants may be derived therefrom by a person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining physiological cardiac parameters as a function of heart rate, the method comprising:
   recording, using an X-ray device, for at least two different heart rates set by cardiac stimulation during recording, a respective four-dimensional image data set of a heart comprising at least an entire cardiac cycle; and
   determining a physiological cardiac parameter, the determining comprising evaluating the four-dimensional image data sets.

2. The method of claim 1, wherein the determining comprises determining the physiological cardiac parameter at least partially in a time-dependent manner, from a dynamic model of the heart, from at least one cardiac parameter related to a heart wall, from at least one cardiac parameter related to a lumen, or a combination thereof, at least one cardiac parameter related to cardiac perfusion is determined as the physiological cardiac parameter, or a combination thereof.

3. The method of claim 2, wherein the determining comprises determining the physiological cardiac parameter from a wall thickness.

4. The method of claim 2, wherein the determining comprises determining the physiological cardiac parameter from a volume of the lumen.

5. The method of claim 1, further comprising determining a Duke score, a WMSI score, a Bowditch effect, a systolic volume index, a cardiac ejection fraction, a contraction force-frequency relationship, or a combination thereof from the physiological cardiac parameter.

6. The method of claim 1, further comprising setting an increase in heart rate in fixed, predefined steps, setting heart rates in a range from 80 to 150 bpm, or a combination thereof.

7. The method of claim 1, further comprising adjusting a heart rate, the adjusting comprising intra-cardiac pacing using a pacing catheter, extracardiac pacing using a cardiac pacemaker, or a combination thereof.

8. The method of claim 1, wherein the recording of the four-dimensional image data sets is carried out after administering contrast agent.

9. The method of claim 8, further comprising recording at least one late-enhancement-image data set for each of the at least two different heart rates.

10. The method of claim 1, wherein the four-dimensional image data sets are calculated by reconstructing a plurality of three-dimensional image data sets out of two-dimensional projection images for different projection directions recorded at the same phase of the cardiac cycle using the X-ray device and by combining the three-dimensional image data sets, the X-ray device comprising a recording arrangement, the recording arrangement comprising an X-ray detector and an X-ray emitter.

11. The method of claim 10, wherein recording of the projection images for various cardiac phases is carried out during one rotation of the recording arrangement, a recording parameter describing a temporal progression during the recording of the projection images for a heart rate being selected as a function of the heart rate such that the recording of the projection images is synchronized with the cardiac cycle.

12. The method of claim 10, wherein for each heart rate of the at least two different heart rates set, a rotational movement of the recording arrangement covering predefined projection directions is carried out.

13. The method of claim 12, wherein opposing movement directions of the recording arrangement are used in each case for consecutive recordings at different heart rates.

14. The method of claim 10, wherein the projection images for all heart rates are recorded during a single continuous rotation of the recording arrangement.

15. The method of claim 10, wherein the change in heart rate is carried out during the movement of the recording arrangement.

16. The method of claim 10, wherein projection images from other cardiac phases, other heart rates, or other cardiac phases and other heart rates are taken into consideration in the reconstruction of the plurality of three-dimensional image data sets.

17. The method of claim 16, wherein a comparative reconstruction is carried out taking into consideration all the projection images for a heart rate, all the projection images for a cardiac phase at all heart rates, or a combination thereof.

18. The method of claim 16, further comprising reducing a dose, for at least one recording procedure after the recording for a first heart rate of the at least two different heart rates, in comparison with the recording for the first heart rate, at least projection images from records for the first heart rate being taken into account in the reconstruction of the three-dimensional image data sets for later heart rates.

19. The method of claim 18, further comprising reducing the dose, for all recording procedures after the recording for the first heart rate, in comparison with the recording for the first heart rate.

20. The method of claim 1, further comprising segmenting the four-dimensional image data sets.

21. The method of claim 1, further comprising determining cardiac parameters for heart rates that have not been measured, the determining comprising interpolating, extrapolating, or interpolating and extrapolating from the cardiac parameters for measured heart rates, from the four-dimensional image data sets, from heart motion vector fields derived therefrom, or a combination thereof.

22. The method of claim 21, wherein, in an interpolation or extrapolation of motion vector fields of the heart, an interpolation or extrapolation of the image information relating to four-dimensional image data sets is taken into account as a boundary condition, as a penalty component during an optimization procedure, or a combination thereof.

23. An X-ray device comprising:
   a recording arrangement comprising:
      an X-ray emitter;
      an X-ray detector; and
      a control device configured to determine physiological cardiac parameters as a function of heart rate, the control device being configured for:
         recordation, using the recording arrangement, for at least two different heart rates set by cardiac stimulation during recordation, a respective four-dimensional image data set of a heart comprising at least an entire cardiac cycle; and
         determination of a physiological cardiac parameter, the determination of the physiological cardiac parameter comprising evaluation of the four-dimensional image data sets.

24. The X-ray device of claim 23, wherein the recording arrangement further comprises a C-arm.

* * * * *